United States Patent [19]

Sheehan

[11] Patent Number: 4,702,251

[45] Date of Patent: Oct. 27, 1987

[54] WOUND CLOSURE DEVICE

[75] Inventor: Joseph C. M. Sheehan, Burr Ridge, Ill.

[73] Assignee: Kells Medical, Incorporated, Burr Ridge, Ill.

[21] Appl. No.: 698,243

[22] Filed: Feb. 5, 1985

Related U.S. Application Data

[63] Continuation-in-part of Ser. No. 661,375, Oct. 16, 1984, Pat. No. 4,605,005, which is a continuation-in-part of Ser. No. 472,053, Mar. 10, 1983, Pat. No. 4,526,173, which is a continuation-in-part of Ser. No. 367,671, Apr. 12, 1982.

[51] Int. Cl.$^4$ .................. A61B 17/08; A61B 17/04
[52] U.S. Cl. .................. 128/335; 128/334 R
[58] Field of Search ........... 128/335.5, 335, 334 R, 128/334 C

[56] References Cited

U.S. PATENT DOCUMENTS

| | | | |
|---|---|---|---|
| 3,288,137 | 1/1964 | Lund | 128/133 |
| 3,863,640 | 2/1975 | Haverstock | 128/335 |
| 3,926,193 | 12/1975 | Hasson | 128/335 |
| 3,983,878 | 10/1976 | Kawchitch | 128/335 |
| 4,114,624 | 9/1978 | Haverstock | 128/303 R |
| 4,141,363 | 2/1979 | James et al. | 128/335 |
| 4,423,731 | 1/1984 | Roomi | 128/335 |
| 4,467,805 | 8/1984 | Fukuda | 128/335 |
| 4,535,772 | 8/1985 | Sheehan | 128/335 |
| 4,539,990 | 9/1985 | Stivala | 128/335 |
| 4,605,005 | 8/1986 | Sheehan | 128/335 |

OTHER PUBLICATIONS

"Skin Closure Manual" by Kells Medical Inc., Dated 1982.

Primary Examiner—C. Fred Rosenbaum
Assistant Examiner—C. W. Shedd
Attorney, Agent, or Firm—Willian Brinks Olds Hofer Gilson & Lione Ltd.

[57] ABSTRACT

A wound closure device includes first and second attachment members, each of which defines a concave skin contacting surface shaped to bond adhesively to the skin on a respective side of a wound. A bridge is provided to hold the two attachment members in abutting alignment to close the wound. The attachment members are sufficiently resilient to evert the skin on both sides of the wound to bring the skin into healing alignment across the wound. In this way, both the epidermis and the germinal layer or dermis of the skin can be aligned properly to minimize scar tissue formation.

17 Claims, 16 Drawing Figures

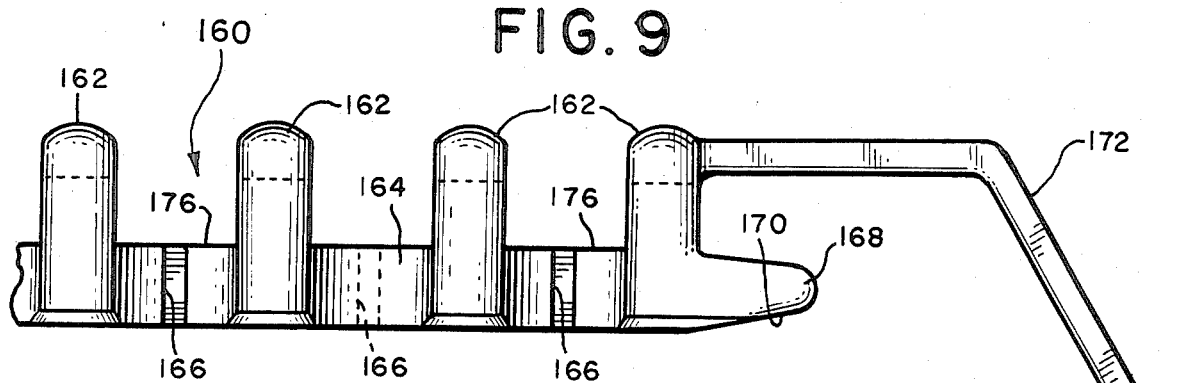
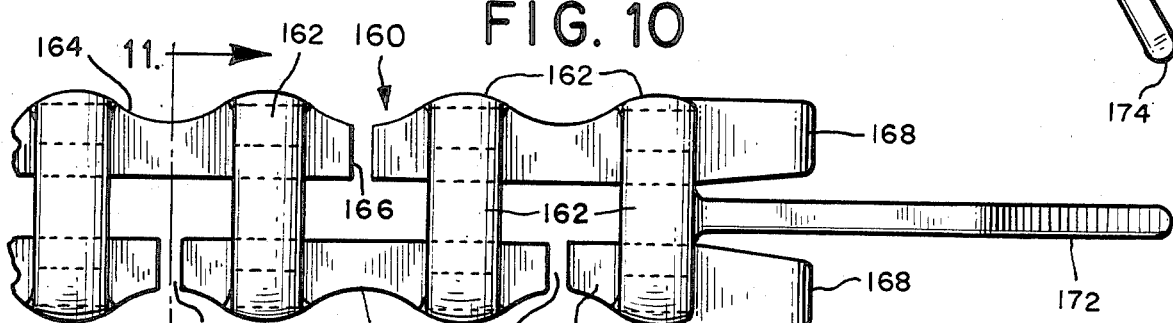
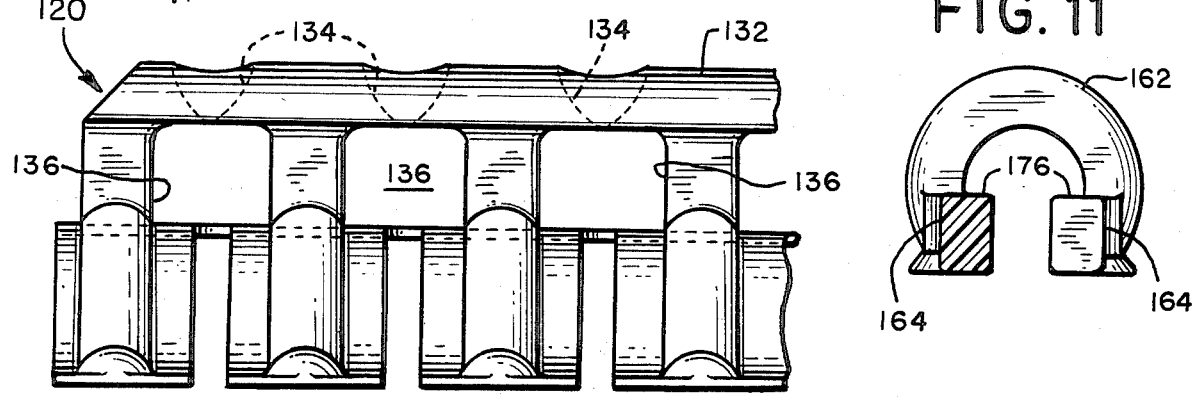
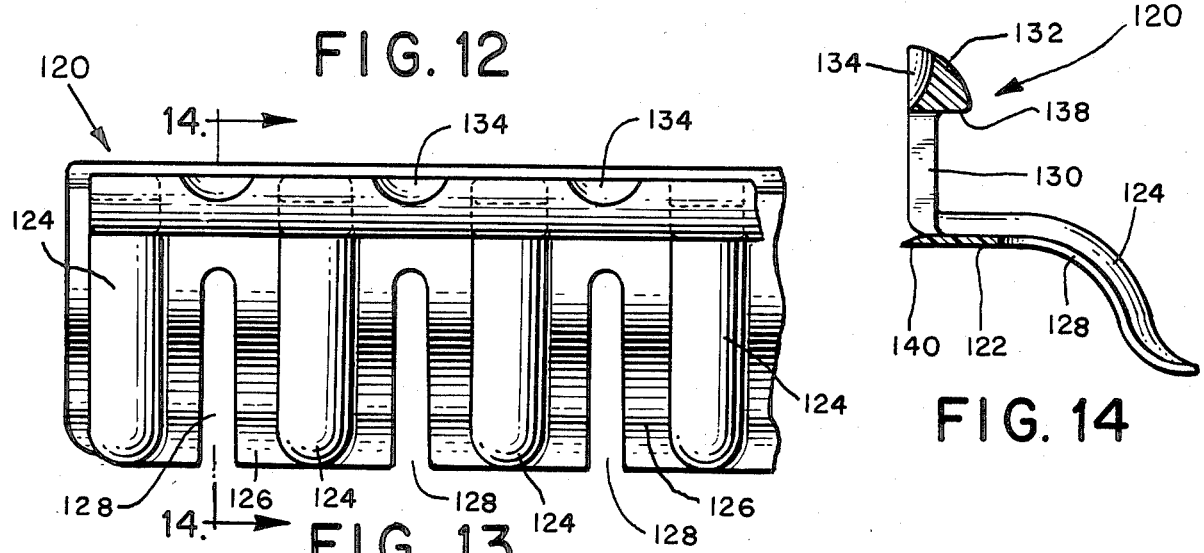

WOUND CLOSURE DEVICE

CROSS-REFERENCE TO RELATED APPLICATION

This application is a continuation-in-part of co-pending application Ser. No. 661,375, filed Oct. 16, 1984, now U.S. Pat. No. 4,605,005, which is in turn a continuation-in-part of co-pending application Ser. No. 06/472,053, filed Mar. 10, 1983, now U.S. Pat. No. 4,526,173, which is in turn a continuation-in-part of application Ser. No. 367,671, filed Apr. 12, 1982, which is still pending.

BACKGROUND OF THE INVENTION

The present invention is directed to an improved adhesive wound closure device which operates to evert the skin adjacent to the wound in order to reduce the formation of scar tissue.

As discussed in detail in the above-identified related applications, the skin is a complex structure which is made up of a number of distinct layers, including the epidermis or outer skin layer and the dermis, or germinal layer. It is the dermis or germinal layer which is the area of skin growth, and as pointed out in the above-identified related applications, remarkable reduction in scar tissue formation can be achieved by bringing both the epidermis and the germinal layer into proper alignment across the wound during wound closure. The full text of the related applications identified above is hereby incorporated by reference in this specification, and these related applications should be referenced for a more complete discussion of the nature of the various skin layers and the importance of bringing both the epidermis and the germinal layer into proper alignment in wound closure.

The earliest two related applications identified above disclose a number of wound closure devices which utilize both surfaces which are adhesively bonded to the epidermis and pins which are mechanically engaged to the dermis in order to achieve the desired alignment of both the epidermal and the germinal layers of the skin during wound closure. This approach has been found to provide remarkably efficient wound closure which minimizes the formation of scar tissue. However, in some applications, the full combination of adhesively bonded surfaces and mechanically engaging pins may not be required to achieve the desired alignment of the epidermis and dermis.

SUMMARY OF THE INVENTION

The present invention is directed to an improved adhesive wound closure device which enhances alignment of both the epidermis and the germinal layer by everting the skin adjacent to the wound.

According to this invention, a wound closure device is provided for a wound in a region of skin which defines an epidermal layer and a germinal layer. This device includes means for defining first and second concave skin contacting surfaces, each shaped to conform to the epidermal layer. An adhesive layer covers the first and second skin contacting surfaces and is adapted to secure the skin contacting surfaces to the epidermal layer on either side of the wound. Means are provided for holding the first and second skin contacting surfaces in alignment to close the wound and evert the skin on both sides of the wound to enhance alignment of the germinal layer across the wound and thereby reduce scar tissue formation.

In one of the preferred embodiments described below, the skin contacting surfaces are defined by respective attachment members which are releasably held together by a channel sized to mechanically secure the two attachment members together with the skin contacting surfaces in alignment.

The present invention provides the important advantage that by everting the skin in the region of the wound, the tendency of the germinal layer to recoil from the wound is to a large extent counteracted. In this way, the alignment of the germinal layer and the epidermal layer across the wound is enhanced and wound healing is allowed to occur with little scar tissue formation. In the preferred embodiments described below, this important result is achieved without the use of pins or other elements which pierce the skin.

The invention itself, together with further objects and attendant advantages, will best be understood by reference to the following detailed description, taken in conjunction with the accompanying drawings.

BRIEF DESCRIPTION OF THE DRAWINGS

FIG. 9 is a side elevational view of the bridge of the embodiment of FIGS. 6-8.

FIG. 10 is a top plan view of the bridge of FIG. 9.

FIG. 11 is a sectional view taken along line 11—11 of FIG. 10.

FIG. 12 is a side elevational view of one of the attachment members of the embodiment of FIGS. 6-8.

FIG. 13 is a top plan view of the attachment member of FIG. 12.

FIG. 14 is a sectional view taken along line 14—14 of FIG. 13.

DETAILED DESCRIPTION OF THE PRESENTLY PREFERRED EMBODIMENTS

Turning now to the drawings, FIGS. 1-5 show various views of a first preferred embodiment of this invention, and FIGS. 6-14 show various views of a second preferred embodiment. The following discussion will take up these two embodiments in sequence.

THE FIRST PREFERRED EMBODIMENT

Figure 1:
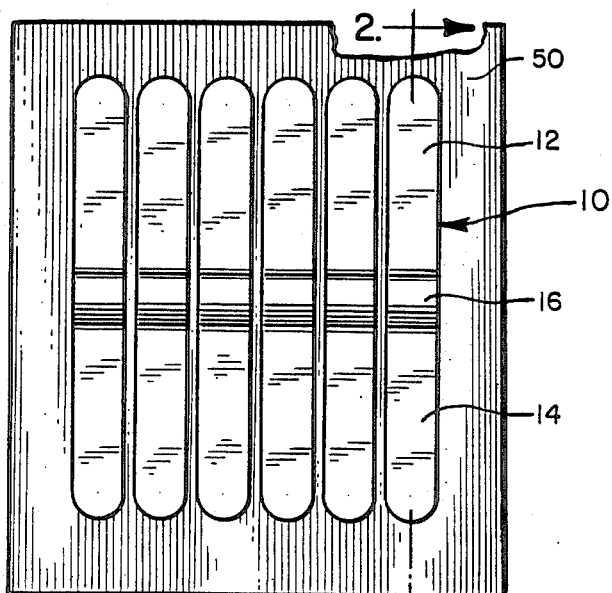
FIG. 1 is a perspective view showing a first preferred embodiment of the wound closure device of this invention.

As shown in FIG. 1, the first preferred embodiment includes a sheet of six separate adhesive strips 10. Each of the strips 10 comprises respective end sections 12,14 disposed on opposite sides of a respective central section 16.

Figure 2:
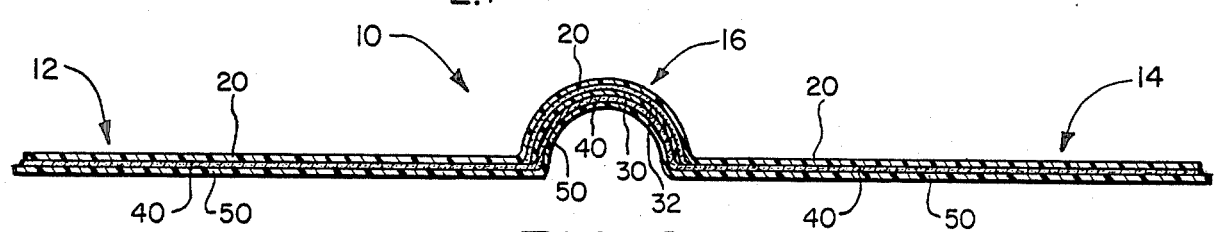
FIG. 2 is a sectional view taken along line 2—2 of FIG. 1.

FIG. 2 shows a cross-sectional view of one of the strips 10. As shown in FIG. 2, each of the strips 10 includes a flexible strip 20 which in this embodiment is a one-piece, flexible, plastic strip which extends over both the end sections 12,14 and the center section 16. A resilient, convexly-curved element 30 is adhesively bonded to the flexible strip 20 in the region of the central section 16 by a layer of adhesive 32. This resilient element 30 has a rest shape which defines a selected convex curvature, which in this preferred embodiment is substantially cylindrical with a radius of curvature of one-fourth inch. As best seen in FIG. 2, the axis of symmetry of the cylindrical curvature of the resilient element 30 is oriented transversely to the length of the strip 10.

An adhesive layer 40 is secured to the exposed surfaces of the underside of both the flexible strip 20 and the resilient element 30. Thus, the adhesive layer 40 extends under both the end sections 12,14 and the central section 16. A backing strip 50 is secured to the exposed surface of the adhesive layer 40 in order to protect the adhesive layer 40 prior to use. The resilient element 30 is deformable such that it can be collapsed or flattened into a planar configuration during application, and will then return to a convex shape as shown in FIG. 4.

Figure 3A:
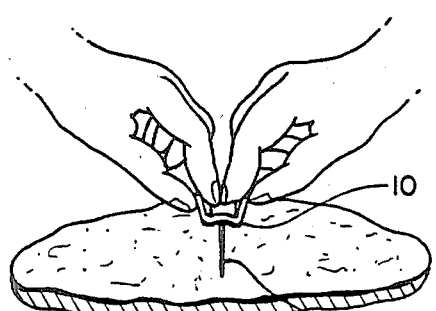
FIGS. 3a-3c are perspective views showing the method of use of the preferred embodiment of FIG. 1.
Figure 3B:
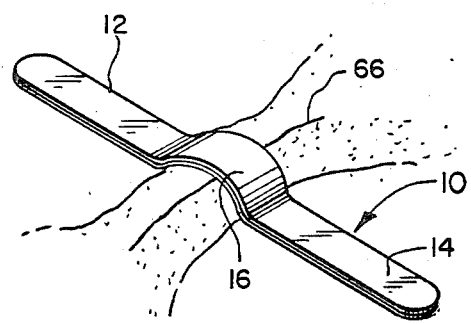
Figure 3C:
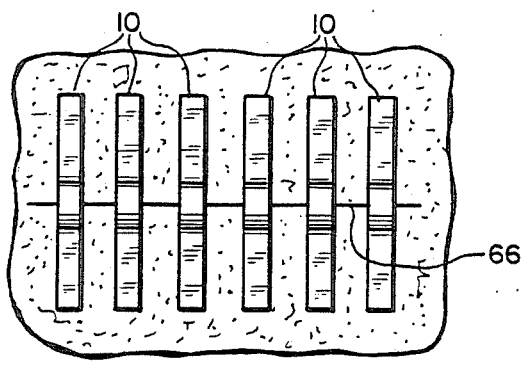

FIGS. 3a–3c are perspective views which illustrate various features of the use of the preferred embodiment of FIGS. 1 and 2. Prior to use, the skin surrounding the wound to be closed is cleaned and dried, and a suitable adhesive can, if desired, be applied over the entire region to be covered by the strip 10. Then, one of the strips 10 is removed from the backing sheet 50 and held with two hands, preferably as shown in FIG. 3a. Index digital pressure is then applied to the central section 16 in order to flatten the central section 16, and the strip then is positioned across the wound to be closed, with slight traction on the ends of the strip 10. The strip 10 is then pressed into position, after the epidermal layer has been brought properly into alignment. If necessary, forceps may be used in the conventional manner to appose the two sides of the wound properly prior to application of the strip 10. In this way, the central section 16 is securely adhesively bonded to the epidermal layer on both sides of the wound immediately adjacent to the marginal edges of the wound. Then the end sections 12,14 are pressed into adhesive engagement with the epidermal layer. Once the strip 10 has been adhesively bonded to the epidermal layer, it is then released. The resilient element 30 returns to the cylindrically convex shape shown in FIG. 4, thereby everting the edges of the skin at the central section 16 adjacent to the wound. FIG. 3b shows the manner in which a single strip 10 can be used to close a small wound and to evert the marginal edges of the skin adjacent to the wound, and FIG. 3c shows the manner in which an array of strips 10 can be used to close a longer wound in a similar manner. It should be noted that in each case the marginal edges of the skin adjacent to the wound are everted.

Figure 4:
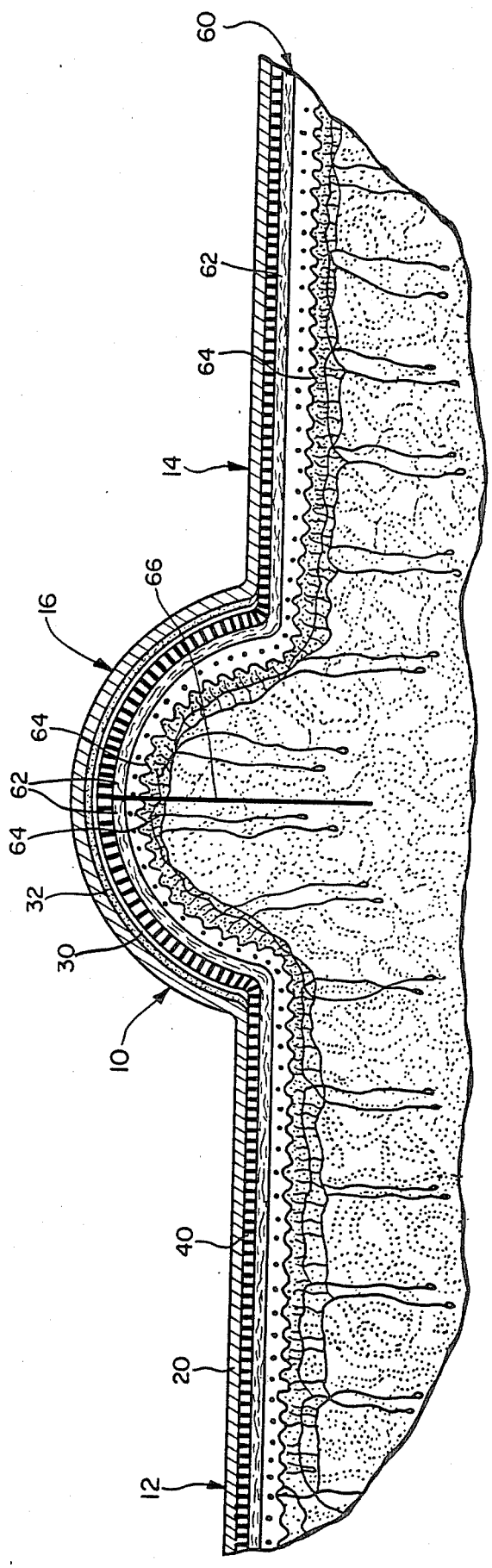
FIG. 4 is a sectional view taken along line 4—4 of FIG. 3b showing the embodiment of FIG. 1 as applied to close a skin wound.

FIG. 4 is a cross-sectional view taken from FIG. 3b which illustrates the importance of everting the marginal edges of the skin. As shown in FIG. 4, the central section 16 is securely adhesively bonded to the epidermal layer 62 adjacent to the wound 66. For this reason, when the resilient element 30 returns to convex shape, it everts the epidermal layer 62. This causes the underlying germinal layer 64 to be everted as well, thereby improving alignment of the germinal layer 64 across the wound 66 and counteracting the natural tendency of the germinal layer 64 to recoil from the wound 66. In this way, the formation of scar tissue is minimized.

It will be understood that a wide range of materials and manufacturing techniques can be used to form the strip 10. However, the following details are provided in order completely to define the presently preferred embodiment of this invention. It should be clearly understood that these details are provided only by way of illustration, and are not intended to be limiting in any way.

In this preferred embodiment, the flexible strip 20 is formed of a polyurethane material and is two and one-half inches in length and one-fourth inch in width. The polyurethane film distributed by J. P. Stevens ampersand symbol Co., Easthampton, Ma., and identified as MP-1880 has been found to be suitable in a thickness of 0.005 inch. Such a polyurethane is sufficiently porous to allow the underlying skin to breathe and to minimize skin maceration. In this embodiment the resilient element 30 is formed of a 0.005 inch co-polyester film such as the material distributed by Eastman Chemical Products, Kingsport, Tenn., under the trade name Kodar. In this embodiment the resilient element 30 is adhesively bonded to the flexible strip 20 by a material such as the adhesive distributed by Fitchburg CPI as Type 594 medical adhesive. The adhesive layer 40 in this embodiment comprises a one-half mill layer of a polyester film which is coated on both sides with a medical adhesive; a suitable material is obtainable from Fitchburg CPI, coated with the above-identified Type 594 medical grade adhesive coated film. One side of this adhesive secures the polyester strip to the exposed surfaces of the flexible strip 20 and the resilient element 30, and the other side of this adhesive coated film secures the entire strip 10 to the epidermal layer of the skin. In this embodiment, the backing sheet 50 is formed of a film such as for example, the material distributed by H. P. Smith, Bedford Park, Ill., as 5 mill Natural H. D. Film-S #2071.

The presently preferred method for manufacturing the strip 10 begins with the lamination of each of the layers described above. Then a die-cut operation is performed to cut the flexible strip 20, the resilient element 30, and the adhesive layer 40 into strips of the desired width. A group of a number of strips 10 all adhesively secured to a single backing sheet 50 is then processed on a conventional heat sealing apparatus. This heat sealing apparatus is used to supply sufficient heat and pressure to form the resilient element 30 into the desired convex shape. The entire strip 10 is then cooled and packed in a suitable container. For example, the container can preferably be formed of the material marketed by DuPont under the trade name Tyvek. This material is permeable to ethylene oxide and the entire packaged assembly can then be sterilized with 100% ethylene oxide. In the heat sealing step, the heat and pressure should be chosen at values high enough to ensure the formation of the desired convex shape in the resilient element 30, yet not so high as to cause the materials in the adhesive layer 40 to flow or shrivel. In alternate embodiments, the heat sealing step can be performed directly during the lamination process.

Preferably, the strip 10 is sufficiently rigid in the central section 16 in order to evert the skin as shown in FIG. 4. Note that a straight line drawn between the points where the central section 16 joins the end sections 12,14 intersects the germinal layer 64. In this way, the desired forces are applied to the germinal layer 64 in order to obtain the desired apposition. In this embodiment, the rigidity of the resilient element 30 should be sufficient to evert the skin as shown in FIG. 4, yet not so rigid as to impede adhesive bonding between the central section 16 and the epidermal layer 62 during application of the strip 10 to the skin. In addition, an excessively rigid central section 16 can result in irritation to the epidermal layer 62 at the region where the central section 16 joins the end sections 12,14.

In a first variant of the first preferred embodiment, at least a center portion of an adhesive strip is made of a rigid material such as aluminum which can be bent to a desired shape after it has been applied to the epidermis across the wound. For example, a thin, flat aluminum strip can be provided with an adhesive layer on one side. Then, after the marginal edges of the wound have been apposed, the adhesive is used to securely bond the entire length of the strip to the skin as described above, with the strip bridging the wound. A forceps or other similar device is then used to bend or shape the strip into approximately the shape shown in FIG. 4 in connection with the first preferred embodiment. Because the aluminum strip is relatively rigid, it holds this curved shape, thereby everting the skin and apposing the germinal layer across the wound as described above in connection with FIGS. 1-4.

This first variant is similar in terms of operation to the embodiment of FIGS. 1-4. However, the preformed, resilient element 30 has been eliminated and replaced by a rigid section which is bent to the desired skin everting shape after the strip has been secured to the skin.

Figure 5:
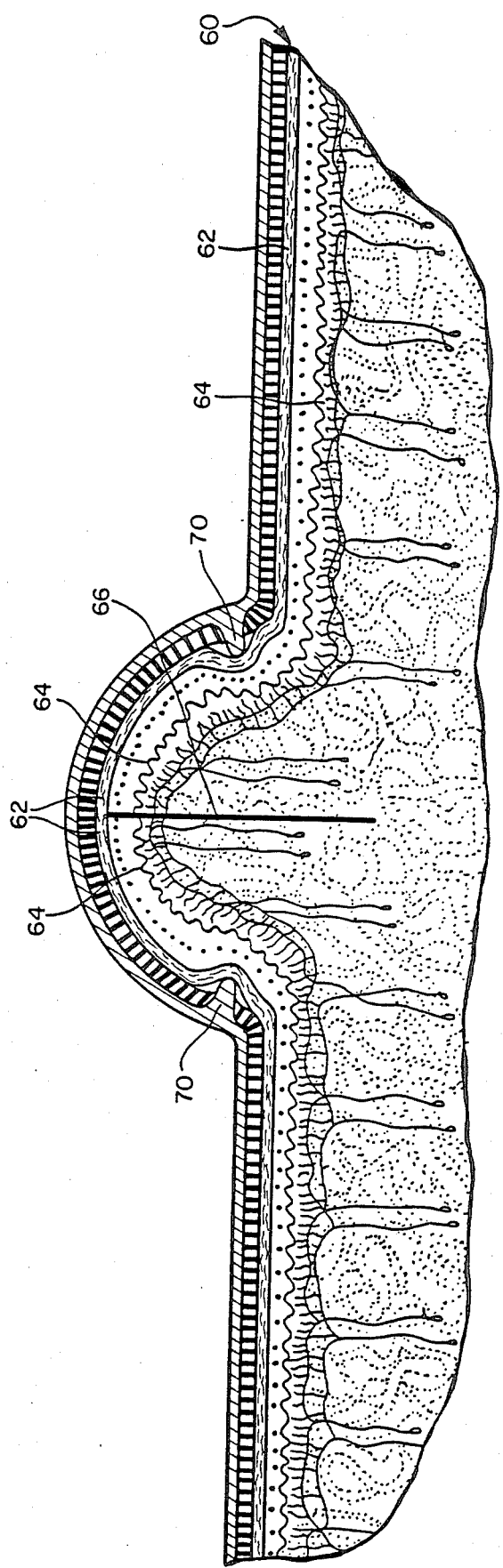
FIG. 5 is a cross-sectional view of a variant of the first preferred embodiment, taken in a plane similar to that of FIG. 4.

FIG. 5 shows a second variant of the first preferred embodiment which is in many ways similar to that of FIGS. 1-4. The principal difference is that the variant of FIG. 5 includes two molded protrusions 70 in the center section, each positioned to engage the skin mechanically without penetrating the skin. In this way slipping of the skin with respect to the strip is further impeded. The protrusions 70 are each about two millimeters in length. If desired, a pair of protrusions may be provided at each end of the center section to impede rotation of the skin under the strip.

THE SECOND PREFERRED EMBODIMENT

FIGS. 6-14 show a second preferred embodiment 110 of the wound closure device of this invention. This second preferred embodiment 110 includes two identical attachment members 120, each of which is adhesively secured in place by an adhesive layer 150. A bridge 160 is used to hold the two attachment members 120 together in order to close a wound.

FIGS. 8 and 12-14 show various views of one of the attachment members 120. Each of these attachment members defines a concave skin contacting surface 122 which is cylindrically concave. The inner longitudinal edge of the skin contacting surface 122 which will overlie the wound 112 is defined by a projecting flange 140. An array of stiffening ribs 124 extends transversely to this flange 140, and a thin web 126 of material is disposed between the ribs 124. As shown in FIGS. 12-13, an array of slits 128 is formed in the web 126 between the ribs 124.

An array of legs 130 extends upwardly away from the skin contacting surface 122. The legs 130 are arranged in spaced, parallel arrangement as shown in FIG. 12, and they define openings 136 between adjacent legs 130. A longitudinally extending rail 132 is connected to the upper ends of the legs 130, and this rail 132 extends parallel to the flange 140. An array of recesses 134 are formed in an inner upper surface of the rail 132, as shown in FIG. 13. The rail 132 defines a locking face 138 which extends substantially transverse to the legs 130.

Each of the skin contacting surfaces 122 is covered with an adhesive layer 150. In this embodiment, the adhesive layer 150 is formed from a sheet of thin plastic having an adhesive on each side. The adhesive on one side secures the thin plastic sheet to the skin contacting surface 122, and the adhesive on the other side secures the attachment member 120 to the skin.

Figure 8:
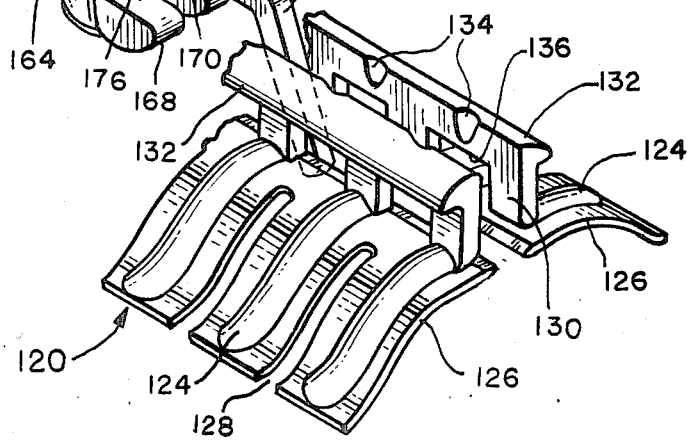
FIG. 8 is an exploded perspective view of the embodiment of FIGS. 6-7.

As shown in FIGS. 8-11, the bridge 160 is a channel-shaped structure having a top wall 162 and two spaced parallel side walls 164. The top wall 162 defines a regular array of openings 165, and each of the side walls 164 defines a regular array of side slits 166. The top openings 165 provide improved wound drainage in cooperation with the recesses 134, and the side slits 166 provide improved lateral flexibility to the bridge 160. One end of the bridge 160 defines a nose section 168 which in turn defines an upwardly sloping tapered surface 170. A flexible probe 172 extends outwardly from this end of the bridge 160 as shown in FIGS. 8-10. This probe 172 defines a free end 174 which extends downwardly toward the wound when the bridge 160 is in use. The bridge 160 defines two parallel locking surfaces 176 which are configured to interlock with the locking faces 138 of the attachment members 120.

Purely by way of example, the following details are provided in order better to define this preferred embodiment. In this embodiment, both the attachment members 120 and the bridge 160 are molded from a high density polyethylene such as that marketed by DuPont under the trade name ALATHON 7050. In this embodiment, the adhesive layer 150 includes a ½ mill polyester film coated on two sides with medical adhesive. A suitable material can be obtained from Fitchburg CPI of Scranton, Pa., utilizing No. 594 medical adhesive. If desired, a release paper such as a silicone-treated paper can be applied over the adhesive layer 150 to protect the adhesive layer 150 prior to use. In order to improve the adhesive bond between the adhesive layer 150 and the skin contacting surface 122, the skin contacting surface 122 may be provided with a textured No. 6 surface. The illustrated embodiment measures approximately 0.30 inch from the flange 140 to the extreme end of one of the ribs 124, transversely the legs 130. The web 126 is approximately 0.005 inch thick, and the slits 128 are cut in the attachment member 120 after the adhesive layer 150 has been applied, such that the slits 128 extend through both the web 126 and the adhesive layer 150.

Figure 6:
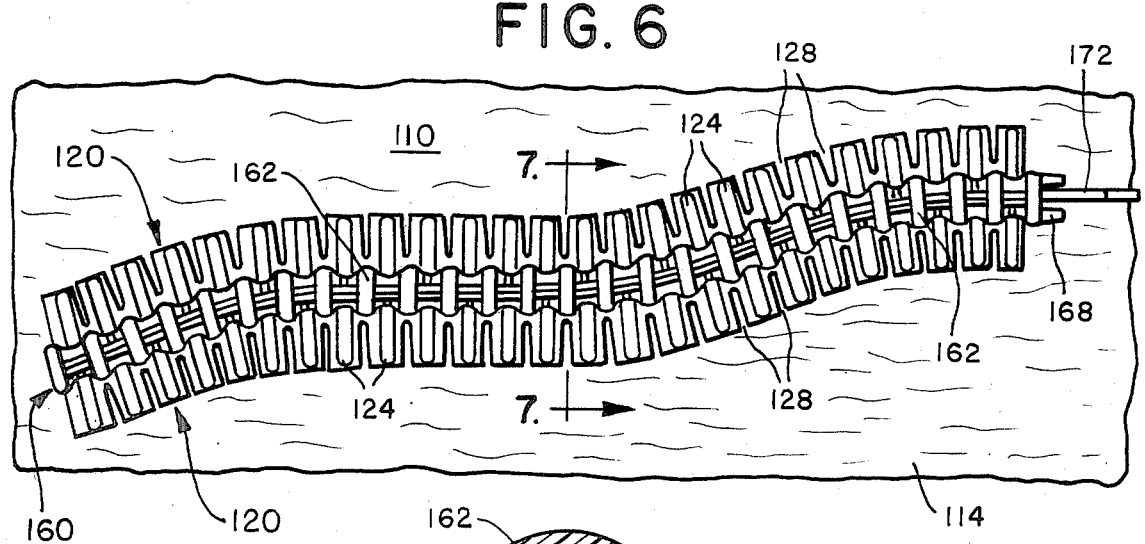
FIG. 6 is a plan view of a second preferred embodiment of this invention in position closing a skin wound.
Figure 7:
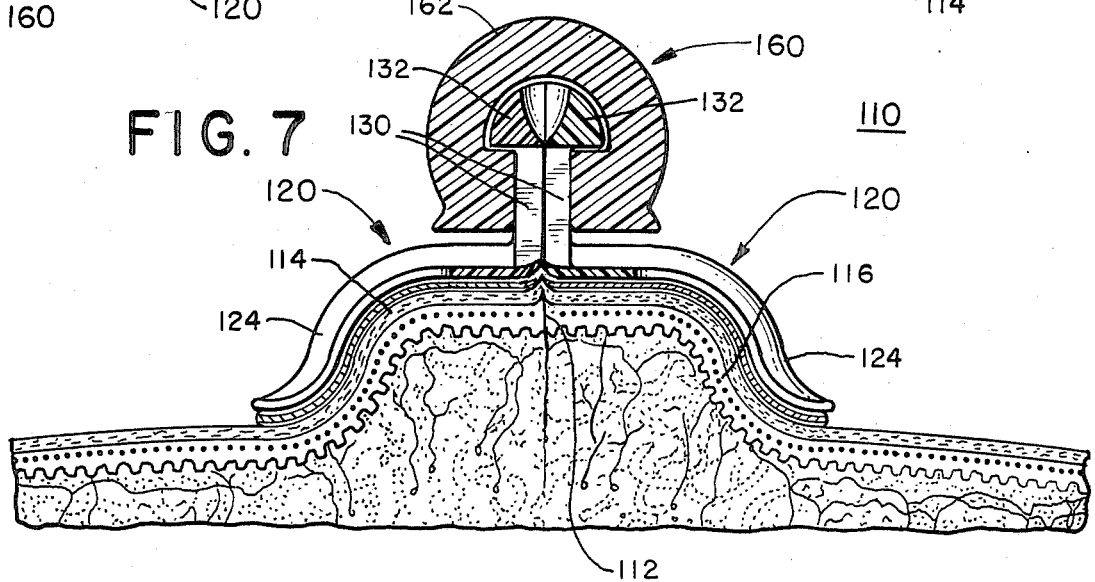
FIG. 7 is a cross-sectional view taken along line 7—7 of FIG. 6.

The embodiment of FIGS. 6-14 can be used to close a skin wound 112 as shown in FIGS. 6-7. In FIG. 7, the reference numeral 114 is used to designate the epidermis, and the reference numeral 116 is used to designate the germinal layer, or dermis. As a first step, a liquid, medical-grade adhesive is applied to the epidermis 114 on either side of the wound 112. A suitable adhesive is that marketed by Dow Corning as No. 355 Medical Adhesive. An attachment member 120 is then applied to the epidermis 114 on either side of the wound 112. The flange 140 can be used as an index to define the precise desired position of the attachment member 120 with respect to the wound 112. Preferably, the attachment member 120 is positioned such that the inward edge of the flange 140 corresponds precisely with the marginal edge of the epidermis 114 adjacent the wound 112.

Once both of the attachment members 120 have been adhesively affixed in place, the bridge 160 is moved over the rails 132 in order to close the wound 112. As the bridge 160 is moved into place, the probe 172 extends into the wound 112, and the free end 174 is bent back toward the nose section 168. In this position, the free end 174 of the probe 172 tends to position the tissue within the wound 112 properly, preventing any such tissue from extending above the epidermis 114. The positive locking engagement between the attachment members 120 and bridge 160 ensures that the attachment members 120 are held together with the skin contacting surfaces in proper alignment.

In applying the attachment members 120 to the epidermis 114, the skin contacting surfaces 120 may be flattened to a considerable extent to ensure positive adhesive bonding between the adhesive layers 150 and the epidermis 114. Because of this positive adhesive bonding, the attachment members 120 evert the skin on either side of the wound 112 when the attachment members are held together as shown in FIG. 7. This eversion of the skin tends to bring the edges of the dermis 116 on either side of the wound 112 into proper alignment, and to counteract the tendency of the dermis 116 to recoil away from the wound 112. The skin contacting surfaces 122 hold the epidermis 114 in precise healing alignment. It has been discovered when both the epidermis 114 and the dermis 116 are properly apposed in edge-to-edge contact, scar tissue formation is remarkably reduced.

From the foregoing, it should be apparent that a number of improved wound closure devices have been disclosed. These wound closure devices are effective alternatives to sutures or staples in many applications. They can be used to assist primary suture or staple closure, or used after suture or staple removal to support and protect the closure. The preferred embodiments described above evert the epidermal layer in order to provide excellent tissue apposition, excellent support and comfort, and substantially unconstricted blood flow to the closure. These embodiments manipulate the skin to sustain tissue eversion and apposition, which are important factors in proper healing. In addition, several of the preferred embodiments described above allow the skin to breathe and allow free wound drainage. It has been discovered that the embodiment described above in connection with FIGS. 1-4 generally results in a reddening of the skin under the strip 10 near the wound, and this reddening is believed to result from increased blood flow near the wound stimulated by the strip.

Of course, it should be understood that a wide range of changes and modifications can be made to the preferred embodiments described above. For example, other materials can be used for the flexible strip 20, such as woven materials including woven polyesters. Furthermore, other materials and dimensions can be changed as needed to fit individual applications. It may be desirable, for example, to form strips or attachment members with varying everting geometries, each matched to skin thickness of a selected body region. It is therefore intended that the foregoing detailed description be regarded as illustrative rather than limiting, and that it be understood that it is the following claims, including all equivalents, which are intended to define the scope of this invention.

I claim:

1. A wound closure device for a wound in a region of skin which defines an epidermal layer and a germinal layer, said device comprising:
    means for defining first and second concave skin contacting surfaces, each presenting a respective concave surface to the epidermal layer;
    an adhesive layer covering the first and second skin contacting surfaces and adapted to secure the skin contacting surfaces to the epidermal layer on either side of the wound to cause the epidermal layer to conform to the concave skin contacting surfaces; and
    means for holding the first and second skin contacting surfaces in alignment to close the wound, to hold the epidermal layer together in alignment across the wound, and to evert the skin on both sides of the wound to enhance alignment of the germinal layer across the wound and thereby reduce scar tissue formation.

2. The invention of claim 1 wherein the means for defining the first and second skin contacting surfaces comprises two attachment members, each comprising a respective rail secured to the respective skin contacting surface to extend along the wound above the skin, and wherein the holding means comprises a channel sized to fit over the rails of the attachment members to hold the rails together.

3. The invention of claim 2 wherein each of the rails is connected to the respective skin contacting surface by an array of spaced, parallel legs.

4. The invention of claim 1 wherein each of the skin contacting surfaces comprises an array of stiffening ribs oriented to extend away from the wound.

5. The invention of claim 1 wherein each of the skin contacting surfaces defines an array of slits oriented to extend away from the wound.

6. A wound closure device for a wound in a region of skin, said device comprising:
    first and second attachment members, each comprising a concave skin contacting surface shaped to bond adhesively to the skin on a respective side of a wound, each of said concave skin contacting surfaces presenting a respective concave surface to the skin;
    an adhesive layer covering the first and second skin contacting surfaces and adapted to secure the skin contacting surfaces to the skin on either side of the wound to cause the skin to conform to the skin contacting surfaces; and
    means for releasably aligning and holding the two attachment members together to close the wound;
    said attachment members being sufficiently resilient to evert the skin on both sides of the wound to bring the skin into healing alignment across the wound.

7. The invention of claim 6 wherein each of the attachment members comprises a rail secured to the skin contacting surface to extend along the wound above the skin, and wherein the holding means comprises a channel sized to fit over the rails of the attachment members to hold the rails together.

8. The invention of claim 7 wherein each of the rails is connected to the respective skin contacting surface by an array of spaced, parallel legs which define drainage openings therebetween.

9. The invention of claim 7 wherein the channel comprises a probe at one end thereof oriented to extend into the wound between the attachment members during wound closure.

10. The invention of claim 7 wherein the channel comprises a top wall and a pair of spaced, depending side walls, and wherein the side walls are slit along the length of the channel to increase lateral flexibility of the channel.

11. The invention of claim 10 wherein the channel defines an array of openings along the top wall.

12. The invention of claim 6 wherein each of the skin contacting surfaces comprises an array of stiffening ribs oriented to extend away from the wound.

13. The invention of claim 6 wherein each of the skin contacting surfaces defines an array of slits oriented to extend away from the wound.

14. The invention of claim 6 wherein the skin contacting surfaces each comprise a flange positioned to be placed over the wound, and wherein each of said flanges is bendable.

15. A wound closure device for a wound in a region of skin, said device comprising:
  first and second attachment members, each comprising a cylindrically concave skin contacting surface, an array of upstanding spaced, parallel legs connected to an inner longitudinal edge of the skin contacting surface, and a rail extending parallel to the inner longitudinal edge and connected to the legs, said skin contacting surfaces each defining an array of stiffening ribs extending transversely to the inner longitudinal edge and an array of slits, each extending between an adjacent pair of ribs, said skin contacting surfaces each presenting a respective concave surface to the skin;
  a layer of adhesive on each of the skin contacting surfaces to secure the skin contacting surfaces to the skin on either side of the wound to cause the skin to conform to the skin contacting surfaces;
  a bridge shaped to slide over the rails of the attachment members to hold the attachment members together with the skin contacting surfaces in alignment to hold the skin together in alignment across the wound, said bridge comprising a top wall which defines an array of spaced apertures and a pair of parallel side walls, each defining an array of spaced openings;
  said skin contacting surfaces shaped to evert the skin on both sides of the wound when adhesively secured to the skin.

16. The invention of claim 15 wherein the bridge comprises a probe at one end thereof oriented to extend into a wound between the attachment members during wound closure.

17. The invention of claim 15 wherein the skin contacting surfaces each comprise a flange positioned to be placed over the wound, and wherein each of said flanges is bendable.

* * * * *